United States Patent [19]

Sundeen

[11] Patent Number: 4,684,722

[45] Date of Patent: Aug. 4, 1987

[54] MONOSULFACTAMS

[75] Inventor: Joseph E. Sundeen, Yardley, Pa.

[73] Assignee: E. R. Squibb & Sons, Inc., Princeton, N.J.

[21] Appl. No.: 816,475

[22] Filed: Jan. 6, 1986

[51] Int. Cl.<sup>4</sup> .................. C07D 417/12; C07D 417/14; C07D 277/38; A61K 31/425

[52] U.S. Cl. ..................................... 540/203; 540/355; 548/194; 548/195; 548/475; 560/351; 560/172; 560/168; 560/160; 560/157; 562/574; 562/560; 562/440

[58] Field of Search ............................... 540/203, 355

[56] References Cited

U.S. PATENT DOCUMENTS

| 4,399,131 | 8/1983 | Dürckheimer et al. ............. 544/27 |
| 4,423,213 | 12/1983 | Takaya et al. ........................ 544/16 |
| 4,533,660 | 8/1985 | Gordon et al. ..................... 540/355 |

FOREIGN PATENT DOCUMENTS

| 127992 | 12/1984 | European Pat. Off. . |
| 58-113174 | 7/1983 | Japan ................... 540/355 |
| 58-206589 | 12/1983 | Japan ................... 540/355 |

1602725 11/1981 United Kingdom .

Primary Examiner—Mark L. Berch
Attorney, Agent, or Firm—Lawrence S. Levinson; Donald J. Barrack

[57] ABSTRACT

Antibacterial activity is exhibited by monocyclic β-lactam antibiotics having in the 1-position an —O—SO$_3$H activating group and in the 3-position an acylamino group of the formula

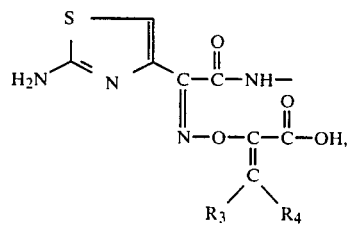

wherein R$_3$ and R$_4$ are each independently hydrogen or alkyl.

12 Claims, No Drawings

MONOSULFACTAMS

BRIEF DESCRIPTION OF THE INVENTION

Compounds having the formula

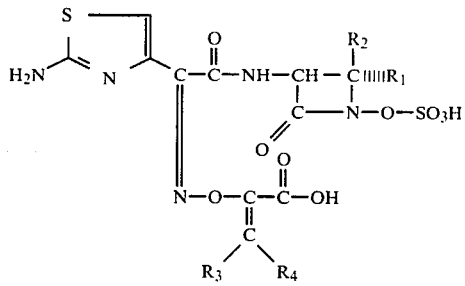

and pharmaceutically acceptable salts thereof, have antibacterial activity. In formula I, and throughout the specification, the symbols are as defined below.

$R_1$ and $R_2$ are the same or different and each is hydrogen or alkyl, or $R_1$ and $R_2$ together are —$(CH_2)_n$— wherein n is 2, 3, 4, 5 or 6; and $R_3$ and $R_4$ are the same or different and each is hydrogen or alkyl of 1 to 3 carbon atoms.

The term "alkyl", unless otherwise defined, refers to both straight and branched chain groups. Those groups having 1 to 10 carbon atoms are preferred.

The compounds of this invention form basic salts with inorganic and organic bases which are also within the scope of this invention. Such salts include ammonium salts, alkali metal salts, alkaline earth metal salts, and salts with organic bases such as dicyclohexylamine, benzathine, N-methyl-D-gluccamine, hydrabamine and the like.

The compounds of this invention are pictured as acids. They can also exist, however, as zwitterions (internal or inner salts), and these are also included within the language "pharmaceutically acceptable salts" and the scope of this invention.

DETAILED DESCRIPTION OF THE INVENTION

The β-lactams of formula I, and pharmaceutically acceptable salts thereof, have activity against gram-positive and gram-negative organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular and as a suppository.

The compounds of this invention can be prepared from a compound having the formula

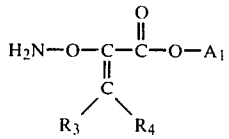

wherein "$A_1$" is a carboxyl protecting group. Carboxyl protecting groups are well known in the art, and are used to prevent involvement of the carboxyl group in subsequent reactions. Exemplary groups used to protect carboxyl groups are described in U.S. Pat. No. 4,144,333, issued Mar. 13, 1979. Preferred groups are t-butyl, diphenylmethyl and phenylmethyl. Removal of a carboxyl protecting group can be accomplished using art-recognized procedures that will vary depending on the particular protecting group. For example, if the protecting group is t-butyl, it can be removed using trifluoroacetic acid, dichloromethane and anisole, using trifluoroacetic acid and thioanisole, or using trimethylsilyliodide and an acid scavenger such as N-methyl-N-(trimethylsilyl)trifluoroacetamide. If the protecting group is diphenylmethyl, it can be removed using trifluoroacetic acid, dichloromethane and anisole. If the protecting group is phenylmethyl, it can be removed using trifluoroacetic acid and thioanisole, or trimethylsilyliodide and an acid scavenger such as N-methyl-N-(trimethylsilyl)trifluoroacetamide. The compounds of formula II are novel, and as such, form an integral part of this invention.

Reaction of a compound of formula II with 2-amino-4-thiazolylglyoxylic acid (or an amino protected derivative thereof) yields a compound having the formula

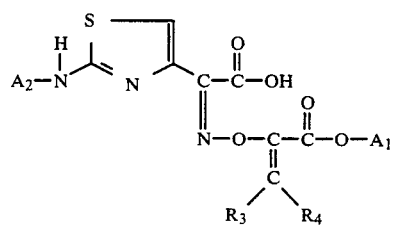

wherein $A_2$ is hydrogen or an amino protecting group. Amino protecting groups are well known in the art, and are used to prevent involvement of the amino group in subsequent reactions. Exemplary amino protecting groups are aromatic acyl groups such as p-nitrobenzyl and p-tert-butylbenzoyl; aliphatic acyl groups such as formyl, acetyl, propionyl, monochloroacetyl, dichloroacetyl, trichloroacetyl and trifluoroacetyl; esterified carboxyl groups such as methoxycarbonyl, ethoxycarbonyl, t-butoxycarbonyl, isopropoxycarbonyl, 2-cyanoethoxycarbonyl, β,β,β-trichloroethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl and phenyloxycarbonyl; methylene groups such as (hexahydro-1H-azepin-1-yl)methylene; sulfonyl groups such as 2-amino-2-carboxyethylsulfonyl; and amino-protecting groups other than acyl groups, such as trityl, 2-nitrophenylthio, di- or trialkylsilyl, benzyl and p-nitrobenzyl. The carboxylic acid of formula III is a novel compound, and as such, forms an integral part of this invention.

Coupling a carboxylic acid of formula III with a β-lactam having the formula

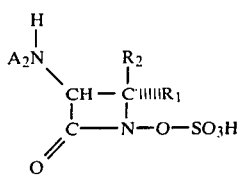   IV yields the corresponding compound having the formula

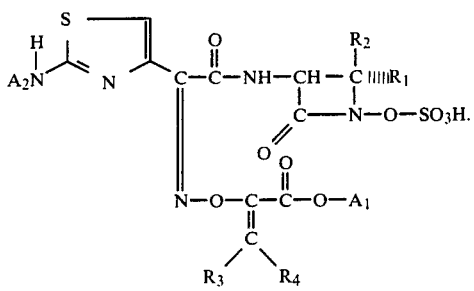   V

The reaction proceeds most readily if the carboxylic acid is in an activated form. Activated forms of carboxylic acids are well known in the art and include acid halides, acid anhydrides (including mixed anhydrides), activated acid amides and activated acid esters. Deprotection of a compound of formula V using art-recognized procedures yields the corresponding product of formula I.

Alternatively, a compound of formula II can be reacted with a glyoxylic acid having the formula

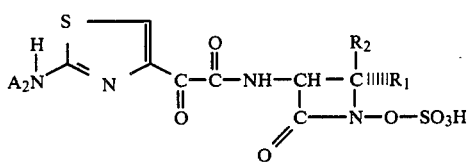   VI to yield the corresponding compound of formula V which can be deprotected to yield the corresponding product of formula I.

Alternatively, the compounds of formula I can be prepared by deprotecting a compound of formula II using art-recognized procedures, yielding the product having the formula

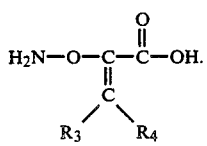   VII

Compounds of formula VII are novel and as such constitute an integral part of this invention.

A compound of formula VII can be reacted with a compound of formula VI to give a compound of formula I after optional deprotection.

The β-lactams of formula IV can be prepared by first coupling a compound having the formula

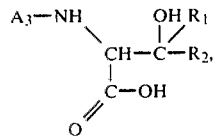   VIII wherein $A_3$ is an amino protecting group, preferably t-butoxycarbonyl or benzyloxycarbonyl, with an O-protected hydroxylamine having the formula

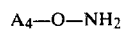   IX wherein $A_4$ is a protecting group such as benzyl, trityl or pivaloyl, yielding the corresponding compound having the formula

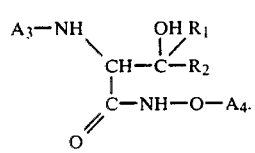   X

The reaction proceeds in the presence of a coupling agent (e.g., 1-ethyl-3-(dimethylaminopropyl)carbodiimide, dicyclohexylcarbodiimide or dicyclohexylcarbodiimide/N-hydroxybenzotriazole).

Reaction of a compound of formula X with pyridine (optionally substituted)-sulfur trioxide complex having the formula

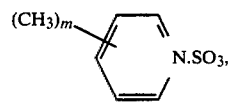   XI wherein m is 0, 1, 2 or 3, yields the corresponding compound having the formula

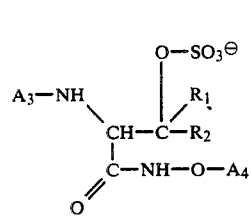   XII

The sulfonation reaction can be run in an organic solvent (e.g., pyridine, mono-, di- or trimethylpyridine, dichloromethane, 1,2-dichloroethane, acetonitrile, dimethylformamide or dioxane).

Cyclization of a compound of formula XII can be accomplished by treatment with a base, and yields the corresponding compound having the formula

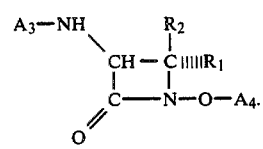   XIII

The base is preferably an inorganic base such as an alkali metal carbonate and the reaction can be run in a mixture of water and an organic solvent (e.g., ethyl acetate, methyl butyl ketone, pyridine or mono-, di- or trimethylpyridine).

Removal of the $A_4$ protecting group from a compound of formula XIII yields the corresponding compound having the formula

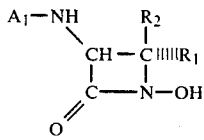
XIV and can be accomplished using art-recognized techniques. For example, if $A_4$ is benzyl, deprotection can be accomplished by catalytic hydrogenation. If $A_4$ is pivaloyl, deprotection can be accomplished by treatment with a base such as sodium sulfide or sodium hydroxide. If $A_4$ is trityl, deprotection can be accomplished by treatment with 80% aqueous acetic acid.

A compound of formula XIV can be treated with a pyridine (optionally substituted)-sulfur trioxide complex of formula XI to yield the pyridinium salt of the corresponding compound having the formula

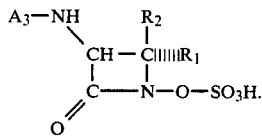
XV

The reaction can be run in a solvent such as pyridine (optionally substituted), dichloromethane or 1,2-dichloroethane. Using conventional techniques (e.g., ion-exchange resins) the pyridinium salt formed above can be converted to other salts and the free acid.

Those compounds of formula IV wherein $A_2$ is hydrogen are obtained by deprotection of the corresponding compound of formula XV. The deprotection procedure used will depend on the particular protecting group. If, for example, the protecting group is t-butoxycarbonyl, trifluoroacetic acid can be used to deprotect the amino group. If the protecting group is benzyloxycarbonyl, catalytic hydrogenation can be used.

The β-lactams of formula IV can also be prepared using the methodology described in U.S. Pat. No. 4,337,197, issued June 29, 1982. Using the acylation techniques described in the patent, one can also prepare compounds of formula VI.

The amino acids of formula VIII are either known or are readily obtainable using art-recognized procedures; see, for example, *J. Org. Chem.*, 44, 3967(1979); *J. Org. Chem.*, 46, 2809(1981); *Z. Chem.*, 10, 393(1970); *Tetrahedron*, 39, 2085(1983); *Liebigs Annalen der Chem.*, 763, 1(1972); *Synthesis*, 216(1979); *Bull. Chem. Soc. Japan*, 39, 2287(1966). Those procedures include the reaction (an aldol condensation) of protected glycine (both amino and carboxyl groups are protected) with the appropriate ketone

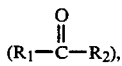

followed by removal of the carboxyl protecting group.

The compounds of formula II wherein "$A_1$" is t-butyl and $R_3$ and $R_4$ are each hydrogen can be prepared by treating a compound having the formula

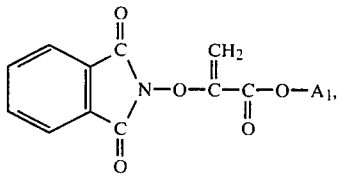
XVI with hydrazine or methylhydrazine. The compound of formula XVI wherein $A_1$ is t-butyl is known; see, for example, Belgian Pat. No. 866,422. By methods known in the art, the t-butyl group can be removed and replaced with an alternate protecting group such as diphenylmethyl or phenylmethyl.

A compound of formula II can be prepared from a ketone or aldehyde having the formula

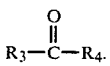
XVII

Reaction of a compound of formula XVII with an α-haloacetate ester (e.g., ethyl chloroacetate) in the presence of a strong base (e.g., potassium t-butoxide) and subsequent hydrolysis of the resulting glycidic ester (see *J. Org. Chem.*, 26:3176 (1961)) yields a salt of the corresponding compound having the formula

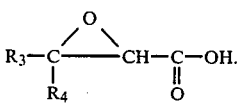
XVIII

Alternatively, a compound of formula XVIII can be prepared from a salt of a compound having the formula

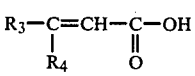
XIX by treatment with aqueous hydrogen peroxide in the presence of catalytic sodium tungstate (see *J. Org. Chem.*, 50:1979 (1985)).

Treatment of a compound of formula XVIII with a reagent such as acetone oxime, benzaldehyde oxime, p-methoxybenzaldehyde oxime or t-butyl N-hydroxy carbamate in the presence of a base (e.g., an alkali metal hydroxide) in a solvent (e.g., water, water/dioxane, water/dimethylsulfoxide, water/ethanol, ethanol, dimethylformamide, or dimethylsulfoxide) yields a compound having the formula

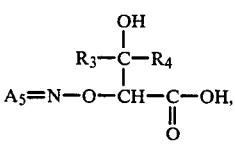
XX wherein $A_5$ is isopropylidene, benzylidene or p-methoxybenzylidene, or "$A_5=N-$" is t-butoxycarbonylamino. If $A_5$ is isopropylidene, benzylidene, or p-methoxybenzylidene, conversion of a compound of formula XX to a compound having an alternate protecting group (e.g., $A_5$ is phthaloyl or the group "$A_5=N$" is t-butoxycarbonylamino) can be achieved by removing the protecting group with a mineral acid in the presence of water and replacing it with the alternate protecting group using art-recognized techniques. If "$A_5=N-$" is t-butoxycarbonylamino, conversion of a compound of formula XX to a compound having an alternate protecting group can be achieved by removing the protecting group with trifluoroacetic acid and anisole and replacing it with the alternate protecting group using art-recognized techniques.

Esterification of a compound of formula XX (or a compound corresponding thereto with a different protecting group) with a carboxyl protecting group $A_1$ yields the corresponding compound having the formula

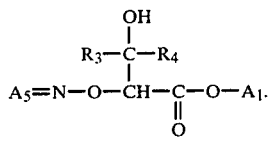    XXI

Dehydration of a compound of formula XXI using any one of a number of art-recognized techniques yields the corresponding compound having the formula

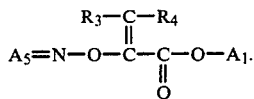    XXII

For example, dehydration can be achieved by treatment of a compound of formula XXI with methanesulfonyl chloride in the presence of two or more equivalents of triethylamine. Alternatively, treatment of a compound of formula XXI with methanesulfonyl chloride in the presence of one equivalent of triethylamine, isolation of the corresponding mesylate, and finally elimination by treatment with an inorganic base (such as potassium carbonate) in an organic solvent (such as dimethylformamide) yields a compound of formula XXII. Alternatively, compound XXI can be converted to a compound having formula XXII using a reagent such as thionyl chloride/pyridine, phosgene/pyridine, or diethylaminosulfur trifluoride/pyridine.

Selective deprotection of a compound of formula XXII to yield the desired compound of formula II can be accomplished using art-recognized techniques. Alternatively, art-recognized deprotection techniques can be used to convert a compound of formula XXII to the corresponding compound of formula VII.

In the above-described synthetic procedures for the preparation of a compound of formula II or III, a compound of formula XVIII wherein $R_4$ is trans to the carboxyl moiety will result in a compound of formula I wherein $R_4$ is cis to the carboxyl moiety.

Alternatively, a compound of formula II or VII (wherein one of $R_3$ and $R_4$ is hydrogen and the other is alkyl of 1 to 3 carbon atoms) can be prepared from an amino acid having the formula

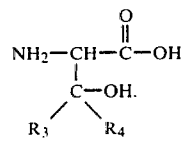    XXIII

Conversion of a compound of formula XXIII to the corresponding benzyl ether can be accomplished using conventional methodology and yields a compound having the formula

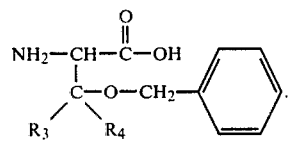    XXIV

Reaction of a compound of formula XXIV with nitrous acid in the presence of bromide ion yields the corresponding compound having the formula

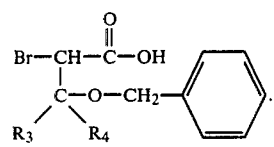    XXV

A compound of formula XXV can be esterified with, for example, a t-butyl group using conventional methodology to yield the corresponding compound having the formula

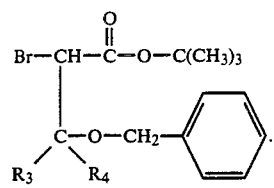    XXVI

Reaction of a compound of formula XXVI with N-hydroxyphthalimide in the presence of a base such as potassium carbonate in dimethylformamide yields a compound having the formula

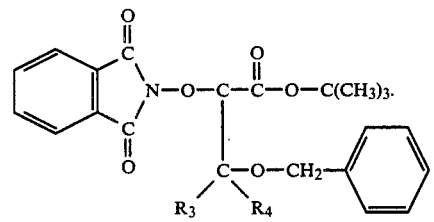    XXVII

Removal of the benzyl protecting groups by hydrogenolysis followed by dehydration yields a compound having the formula

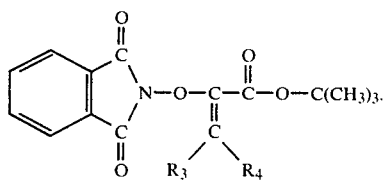

XXVIII

Using methods known in the art, the t-butyl group of a compound of formula XXVIII can be replaced with an alternate protecting group such as diphenylmethyl to yield a compound having the formula

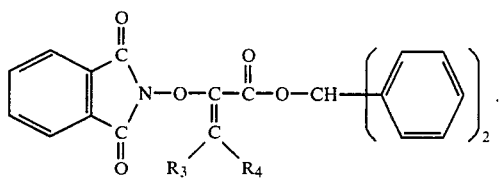

XXIX

Treatment of a compound of formula XXIX with hydrazine or methylhydrazine yields the corresponding compound of formula II wherein $A_1$ is diphenylmethyl. Standard deprotection and protection techniques can be used to convert that compound to other compounds of formulas II and VII.

Alternatively, a compound of formula XXVI can be converted to the corresponding compound having the formula

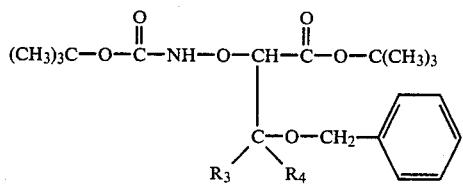

XXX by treatment with t-butyl-N-hydroxycarbamate in the presence of a base such as sodium hydride in a solvent such as dimethylformamide.

Removal of the benzyl protecting group from a compound of formula XXX by hydrogenolysis, and subsequent dehydration, yields a compound having the formula $$(CH_3)_3C-O-\overset{O}{\underset{\|}{C}}-NH-O-\underset{\underset{R_3 \quad R_4}{\overset{\|}{C}}}{C}-\overset{O}{\underset{\|}{C}}-O-C(CH_3)_3.$$

XXXI

Standard deprotection and protection techniques can be used to convert a compound of formula XXXI to a compound of formula II which can optionally be readily converted to the corresponding compound of formula VII.

Using the above methodology, a compound having the geometry

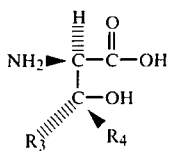

XXXII will yield a compound having the geometry $$NH_2-O-\underset{\underset{R_3 \quad R_4}{C}}{C}-\overset{O}{\underset{\|}{C}}-OH.$$

XXXIII

Alternatively, a compound having the formula $$HC-\overset{O}{\underset{\|}{C}}-OH,$$
$$\underset{\underset{R_3 \quad R_4}{C}}{\|}$$

XXXIV wherein one of $R_3$ and $R_4$ is hydrogen and the other is alkyl of 1 to 3 carbon atoms, can be converted to a compound of formula XXVIII by methodology analogous to that used in the preparation of compounds of formula XVI and described in Belgian Pat. No. 866,422.

A compound having the geometry of formula XXXIV wherein $R_4$ is cis to the carboxyl group will be converted to a compound of formula XXXIII wherein $R_4$ is cis to the carboxyl group.

The compounds of formula I contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G). The compounds of formula I contain the group $$\underset{-\overset{\|}{C}-}{\overset{R_3-C-R_4}{\|}}$$

and can, if $R_3$ and $R_4$ are different, exist as the syn or anti isomer or as a mixture of isomers. All of these isomeric forms are within the scope of this invention.

The compounds of formula I have the imino substituent $$-\underset{N}{\overset{-C-}{\|}}$$

and can, therefore, exist as the syn or anti isomer or as a mixture of isomers. All of these isomeric forms are within the scope of this invention. In general, however, the syn isomer of a compound of formula I has the greatest activity.

The following example is a specific embodiment of this invention.

EXAMPLE 1

(±)-(Z)-2-[[[1-(2-Amino-4-thiazolyl)-2-[[4,4-dimethyl-2-oxo-1-(sulfooxy)-3-azetidinyl]amino]-2-oxoethylidene]amino]oxy]-2-propenoic acid

(A) 2-(1,3-Dioxo-2H-isoindol-2-yl)oxy]-2-propenoic acid

A solution of 2-[(1,3-dioxo-2H-isoindol-2-yl)oxy]-2-propenoic acid, t-butyl ester (1.75 g, 5.7 mmole) in methylene chloride (10 ml) and anisole (10 ml) was treated with trifluoroacetic acid (5 ml). After stirring overnight at room temperature, toluene was added and the reaction mixture was concentrated in vacuo. The residue was triturated twice with hexane to give 1.54 g of the title compound.

(B) 2-[(1,3-Dioxo-2H-isoindol-2-yl)oxy]-2-propenoic acid, diphenylmethyl ester 2-[(1,3-Dioxo-2H-isoindol-2-yl)oxy]-2-propenoic acid (1.54 g, 4.8 mmole) was dissolved in 25 ml of acetonitrile and a solution of diphenyldiazomethane (1.17 g, 5.94 mmole/50 ml acetonitrile) was added dropwise. After approximately 1.1 equivalents of diphenyldiazomethane had been added, tlc showed no starting material remaining. The excess diphenyldiazomethane was decomposed with the addition of a small amount of acetic acid. The reaction solution was concentrated to a residue, dissolved in ethyl acetate, washed consecutively with 1N sodium bicarbonate and brine, dried over anhydrous magnesium sulfate and evaporated to a solid. After trituration with hexane, 1.9 g of the title compound was obtained.

(C) 2-Amino-α-[[[1-(diphenylmethoxy)carbonyl]-ethenyl]oxy]imino]-4-thiazoleacetic acid To a solution of 2-[(1,3-dioxo-2H-isoindol-2-yl)oxy]-2-propenoic acid, diphenylmethyl ester (0.8 g, 2 mmole) in 50 ml of methylene chloride under argon at 0° C. was added hydrazine hydrate (100 mg, 2 mmole in 1 ml absolute ethanol). The reaction mixture was slowly warmed from 0° C. to room temperature over a one hour period and then was stirred at room temperature for an additional two hours. The white precipitate was filtered off and the solution was diluted with diethyl ether and filtered again. The volatiles were then removed from the filtrate to give 2-aminooxy-2-propenoic acid as a residue. The 2-aminooxy-2-propenoic acid was then dissolved in ethanol (6 ml) and water (4 ml) and 2-aminothiazole-4-glyoxylic acid (0.31 g, 1.8 mmol) was added to the solution. After stirring at room temperature for 17 hours, tlc indicated that the reaction was incomplete. Additional ethanol and water were added and a small amount of dimethylformamide was added to solubilize the reactants. After stirring for 72 hours, tlc showed no remaining 2-aminooxy-2-propenoic acid. Evaporation yielded the crude title compound which was chromatographed on an HP20 column eluting with an acetonitrile/water gradient (0 to 80%). Fractions containing the product were concentrated to remove the acetonitrile. Filtration of the resulting aqueous slurry gave the title compound as a precipitate. After drying in vacuo overnight, 167 mg of the title compound was obtained.

(D) N-(t-Butyloxycarbonyl)-$N^2$-(phenylmethoxy)-D,L-3-hydroxyvalinamide

A solution of 24.84 g (106.6 mmol) of N-t-butyloxycarbonyl-D, L-3-hydroxyvaline and 16.33 g (106.6 mmol) of hydroxybenzotriazole monohydrate in 500 ml of dry tetrahydrofuran was cooled to −10° C. and 22 g (106.6 mmol) of dicyclohexylcarbodiimide was added. The mixture was stirred under nitrogen for 1 hour at 0° C. Subsequently, a solution of 13.13 g (106.6 mmol) of 0-benzylhydroxylamine in 250 ml of dry tetrahydrofuran was added over 15 minutes to the activated ester mixture, and the resultant mixture was stirred under nitrogen for 1 hour at 0° C. The insoluble material was filtered away, and the filtrate was evaporated to a foam in vacuo. The foam was extracted with ethyl acetate and more insoluble material was removed by filtration. The filtrate was washed two times with 5% sodium bicarbonate solution. The organic phase was dried (sodium sulfate) and evaporated to a syrup, which was crystallized from 130 ml of isopropyl ether to give 24.7 g of the title compound, melting point 76°–78° C.

(E) N-(t-Butyloxycarbonyl)-$N^2$-(phenylmethoxy)-D,L-3-(sulfooxy)valinamide, pyridinium salt Dry pyridine (8.08 ml, 0.10 mole) was placed in a 500 ml round bottom flask and cooled to −10° C. under nitrogen. Trimethylsilyl chlorosulfonate (15.6 ml, 0.10 mole) was added dropwise (vigorous magnetic stirring) after which the very thick reaction mixture (due to product precipitation) was stirred for 0.5 hours at 0° C. Chlorotrimethylsilane was removed in vacuo yielding 15 g of pyridine-sulfur trioxide complex.

N-(t-Butyloxycarbonyl)-$N^2$-(phenylmethoxy)-D,L-3-hydroxyvalinamide (16.92 g, 50 mmol) was dissolved in 200 ml of dry pyridine, and 9.87 g (62.5 mmol) of pyridine-sulfur trioxide complex was added. The mixture was stirred at 55° C. under nitrogen for 2 hours. Another portion (790 mg, 5 mmol) of pyridine-sulfur trioxide complex was added and stirring was continued for 1 hour longer. The reaction mixture was stripped in vacuo to an oil. The oil was stripped from acetonitrile three times in vacuo to give crude title compound as a foam. The yield was assumed to be quantitative.

(F) (±)-3-[(t-Butyloxycarbonyl)amino]-4,4-dimethyl-1-(phenylmethoxy)-2-azetidinone The flask containing crude N-(t-butyloxycarbonyl)-$N^2$-(phenylmethoxy)-D,L-3-(sulfooxy)valinamide, pyridinium salt (ca. 50 mmol) was placed in an ice bath and 400 ml of ethyl acetate, followed by a solution of 42.8 g (0.31 mole) of potassium carbonate in 90 ml of water, was added with vigorous stirring. The resultant mixture was stirred vigorously under reflux for 2 hours under nitrogen. The reaction mixture was cooled to room temperature and the phases were separated. The aqueous phase was extracted with 2×200 ml of ethyl acetate and all organic phases were combined, dried (sodium sulfate) and evaporated in vacuo. The oil was taken into 40% ethyl acetate/hexane (125 ml) and filtered rapidly through a 350 ml pad (10 cm) of Mallinkrodt SilicAR CC-7 using 3–4 liters of 40% ethyl acetate/hexane. The filtrate was evaporated in vacuo to a solid (12.2 g). Crystallization from 50 ml of isopropyl ether gave 7.15 g of the title compound, melting point 110° C.

(G) (±)-3-[(t-Butyloxycarbonyl)amino]-1-hydroxy-4,4-dimethyl-2-azetidinone (±)-3-[(t-Butyloxycarbonyl)amino]-4,4-dimethyl-1-(phenylmethoxy)-2-azetidinone (8.07 g, 25 mmol) was hydrogenated at atmospheric pressure and ambient temperature in 40 ml of methanol with 0.6 g of 10% palladium on charcoal as catalyst for 2 hours. The reaction mixture was filtered through a pad of Celite and the filtrate was concentrated to yield 5.78 g of the title compound as a solid.

(H) (±)-3-[(t-Butyloxycarbonyl)amino]-4,4-dimethyl-2-oxo-1-azetidinyl sulfate, tetrabutylammonium salt A solution of chlorosulfonic acid (12.27 g, 0.105 mole) in 210 ml of dichloromethane at −40° C. under argon was treated with 20.5 g (0.26 mole) of pyridine dropwise over 10 minutes. The mixture is stirred for 10 more minutes at 0° C. and 10 minutes at 25° C. A slurry of (±)-3-[(t-butyloxycarbonyl)amino]-1-hydroxy-4,4-dimethyl-2-azetidinone in 20 ml of dichloromethane was added and the mixture stirred at 25° C. for 3.5 hours. The nearly homogenous solution was then treated with 250 ml of water and 17 g (0.05 mole) of tetrabutylammonium hydrogen sulfate. The mixture was mixed well and the organic layer separated and dried over sodium sulfate. Evaporation in vacuo gave a foam, which was purified further by dissolution in ethyl acetate, removing insolubles, and evaporation to the title compound as a foam, 30 g.

(I) (±)-3-Amino-4,4-dimethyl-2-oxo-1-azetidinyl sulfate

A solution of 30 g (0.05 mole) of (±)-3-[(t-butyloxycarbonyl)amino]-4,4-dimethyl-2-oxo-1-azetidinyl sulfate, tetrabutylammonium salt in 125 ml of dichloromethane and 10 ml of anisole at −5° C. under argon was treated with 50 ml of trifluoroacetic acid dropwise over 10 minutes. After stirring for 2.5 hours at −5° to 0° C., the mixture was diluted with 50 ml of ethyl acetate and filtered. The solid was washed with dichloromethane and then with ethyl acetate and dried in vacuo to give 9.4 g of the title compound as a white granular solid.

(J) (±)-(Z)-2-[[[1-(2-Amino-4-thiazolyl)-2-[[4,4-dimethyl-2-oxo-1-(sulfooxy)-3-azetidinyl]amino]-2-oxoethylidene]amino]oxy]-2-propenoic acid, diphenylmethyl ester To a solution of 2-amino-α-[[[1-(diphenylmethoxy)-carbonyl]ethenyl]oxy]imino]-4-thiazoleacetic acid(167 mg, 0.4 mmole) and triethylamine (56 μl, 1.0 equivalents) under argon at -30° C. was added diphenyl chlorophosphate (107 mg, 0.4 mmole). The reaction mixture was stirred at −30° C. for one hour to form the mixed anhydride. (±)-3-Amino-4,4-dimethyl-2-oxo-1-azetidinyl sulfate (126 mg, 0.6 mmole) was dissolved in dimethylformamide at 0° C. and this solution and triethylamine (71 μl, 0.85 equivalents) were simultaneously added to the mixed anhydride solution at −30° C. The reaction mixture was stirred for one-half hour at −30° C. and then slowly warmed to 0° C. over a one hour period. The reaction mixture was concentrated in vacuo, taken up in acetone/water and adjusted to pH 6.5 with 1N potassium bicarbonate. A Dowex AG50 (K+) column was run eluting with 30% acetone/water. The appropriate fractions were combined and concentrated and the residual aqueous solution was applied to an HP20 column. The column was eluted with water and then with an acetone/water gradient (0–100%). The appropriate fractions were combined and lyophilized to give the title compound which was all used in the next step.

(K) (±)-(Z)-2-[[[1-(2-Amino-4-thiazolyl)-2-[[4,4-dimethyl-2-oxo-1-(sulfooxy)-3-azetidinyl]amino]-2-oxoethylidene]amino]oxy]-2-propenoic acid To the flask containing (±)-(Z)-2-[[[1-(2-amino-4-thiazolyl)-2-[[4,4-dimethyl-2-oxo-1-(sulfooxy)-3-azetidinyl]amino]-2-oxoethylidene]amino]oxy]-2-propenoic acid, diphenylmethyl ester was added methylene chloride (10 ml) and anisole (10 ml). After cooling to −5° C., trifluoroacetic acid (8 ml) was added and the reaction mixture was stirred at −5 to 0° C. under argon for 45 minutes. Toluene was added, and the reaction mixture was evaporated to a residue. Water and hexane were added to the residue and the layers were separated. The aqueous layer was adjusted to pH 2.5 with 10% potassium bicarbonate. An HP20 column was run eluting first with water and then an acetone/water gradient. The appropriate fractions were combined and lyophilized to give the title compound as a white solid. $^1$H-NMR (1:1 D$_2$O/CD$_3$CN) δ1.57 (s, 3H); 1.75 (s, 3H); 5.09 (s, 1H); 5.75 (d, J = 2.3 Hz, 1H); 5.86 (d, J2.3 Hz, 1H); 7.42 (s, 1H).

EXAMPLE 2

[3S(Z)]-2-[[[1-(2-Amino-4-thiazolyl)-2-[[4,4-dimethyl-2-oxo-1-(sulfooxy)-3-azetidinyl]amino]-2-oxoethylidene]amino]oxy]-2-propenoic acid (A) 2-[(1,3-Dioxo-2H-isoindol-2-yl)oxy]-2-propenoic acid A solution of 2-[(1,3-dioxo-2H-isoindol-2-yl)-oxy]-2-propenoic acid, t-butyl ester (49.9 g, 0.173 mole) in methylene chloride (300 ml) and anisole (150 ml) was treated with trifluoroacetic acid (300 ml). After stirring overnight at room temperature, 800 ml of dry toluene was added and the reaction mixture was concentrated in vacuo. The residue was triturated twice with hexane to give 39.6 g of the title compound.

(B) 2-[(1,3-Dioxo-2H-isoindol-2-yl)oxy]-2-propenoic acid, diphenylmethyl ester

2-[(1,3-Dioxo-2H-isoindol-2-yl)oxy]-2-propenoic acid (39.6 g, 0.17 mole) was dissolved in 800 ml of acetonitrile and a solution of diphenyldiazomethane (43.4 g, 0.224 mole/1000 ml acetonitrile) was added dropwise over 3 hours at 0° C. The reaction solution was evaporated to a solid which was triturated with hexane. The resulting solid was dissolved in dichloromethane and filtered through a pad of silica gel (Kieselgel 60). Addition of hexane produced 47.7 g of the title compound.

(C) 2-Amino-α-[[[1-(diphenylmethoxy)carbonyl]-ethenyl]oxy]imino]-4-thiazoleacetic acid To a solution of 2-[(1,3-dioxo-2H-isoindol-2-yl)oxy]-2-propenoic acid, diphenylmethyl ester (6.07 g, 15.2 mmole) in 375 ml of methylene chloride under argon at 0° C. was added hydrazine hydrate (0.76 g, 15.2 mmole) in 4 ml absolute ethanol. After one hour at 0° C., the mixture was evaporated to dryness at +10° C. and triturated with ethyl ether. Filtration and concentration of the filtrates gave 2-aminooxy-2-propenoic acid, diphenylmethyl ester as a residue. This compound was then treated at 20° C. with a solution of 2-amino-4-thiazoleglyoxylic acid (2.61 g, 15.2 mmole) in dimethylformamide (50 ml), followed by 5 ml of water. The reaction was stirred at 20° C. for 20 hours, and was then chilled and diluted with 250 ml of water. Stirring of the resulting gum gave a granular solid which was filtered, washed with water, and then azeotroped with acetonitrile to dryness. The dry solid was slurried with 100 ml of acetonitrile, filtered, and finally washed sequentially with acetonitrile, ethyl ether, and hexane. Drying in air gave 1.97 g of the title compound.

(D) N-(t-Butyloxycarbonyl)-L-3-hydroxyvaline, α-methylbenzylamine salt

A solution of N-t-butyloxycarbonyl-D,L-3-hydroxyvaline (7.02 g, 30 mmole) in 250 ml of ethyl ether was treated with 3.63 g (30 mmoles) of S-(−)-α-methyl benzylamine. After 8 hours, the resulting solid was filtered. Three recrystallizations from acetonitrile gave 5.80 g of the title compound, melting point 146°–147° C., $[\alpha]_D = -4.5°$ (C=2.0, methanol).

(E) N-(t-Butyloxycarbonyl)-L-3-hydroxyvaline

A mixture of 204.6 g (0.577 mole) of N-(t-butyloxycarbonyl)-L-3-hydroxyvaline, α-methylbenzylamine salt, ethyl acetate (3L) and a solution of 100 g of potassium bisulfate and 150 g of sodium chloride in 1L of water was shaken, the layers separated and the organic phase washed with water and dried over magnesium sulfate. Concentration of the organic solution and trituration with 800 ml of hexane gave 136 g of the title compound, melting point 120°–121° C., $[\alpha]_D = +7.81°$.

(F) N-(t-Butyloxycarbonyl)-N²-(phenylmethoxy)-L-3-hydroxyvalinamide

Following the procedure of Example 1, part D, but substituting N-(t-butyloxycarbonyl)-L-3-hydroxyvaline for N-(t-butyloxycarbonyl)-D,L-3-hydroxyvaline yielded the title compound.

(G) (3S)-3-[(t-Butyloxycarbonyl)amino]-4,4-dimethyl-1-(phenylmethoxy)-2-azetidinone A solution of 2-methylpyridine (296 ml, 3.0 mole) in methyl isobutyl ketone (2700 ml) under argon at −78° C. was treated dropwise with chlorosulfonic acid (80 ml, 1.2 mole) over 30 minutes. After the addition, the mixture was brought to 25° C. over 30 minutes and held there another 30 minutes. To this slurry was added N-(t-butyloxycarbonyl)-N²-(phenylmethoxy)-L-3-hydroxyvalinamide (338.4 g, 1.0 mole) and stirring continued for two hours. To this mixture was added methyl isobutyl ketone (800 ml), $K_2B_4O_7 \cdot 4H_2O$ (1222 g, 4.0 moles), and water (2700 ml), and the mixture was heated to 70° C. While heating, 2N potassium hydroxide (1000 ml, 2 mole) was added dropwise to the mixture over 45 minutes and the mixture was heated for another 55 minutes. The layers were separated and the aqueous phase was extracted with 500 ml of methyl isobutyl ketone. The combined organic layers were chilled to 0° C., washed with 3 L of cold 20% potassium bisulfate, 1L of ice water, and a solution of 50 g of sodium bicarbonate and 100 g of sodium chloride in 1 L of water. The organic layer was dried over sodium sulfate and concentrated in vacuo. The residue was crystallized from 1.75 L of isopropyl ether to yield 161 g of the title compound, melting point 121°–122° C., $[\alpha]_D = +21.06°$ (C =2.55, $CH_2Cl_2$)

(H) (3S)-3-[(t-Butyloxycarbonyl)amino]-1-hydroxy-4,4-dimethyl-2-azetidinone

A solution of 14.77 g (0.0461 mole) of (3S)-3-[(t-butyloxycarbonyl)amino]-4,4-dimethyl-1-(phenylmethoxy)-2-azetidinone in 15 ml of ethanol and 85 ml of ethyl acetate was hydrogenated over 0.75 g of 5% palladium-on-carbon catalyst for 1.5 hours at 1 atmosphere. The reaction mixture was filtered and concentrated to give a white solid. Recrystallization from ethyl acetate gave 8.82 g of the title compound, melting point 148°–149° C., $[\alpha]_D = +31°$ (C =1, ethyl acetate).

(I) (3S)-3-[(t-Butyloxycarbonyl)amino]-4,4-dimethyl-2-oxo-1-azetidinyl sulfate, tetrabutylammonium salt Following the procedure of Example 1, but substituting (3S)-3-(t-butyloxycarbonyl)amino]-1-hydroxy-4 4-dimethyl-2-azetidinone for (±)-3-[(t-butyloxycarbonyl)amino]-1-hydroxy-4,4-dimethyl-2-azetidinone yielded the title compound as a foam.

(J) (3S)-3-Amino-4,4-dimethyl-2-oxo-1-azetidinyl sulfate

Following the procedure of Example 1, part I, but substituting (3S)-3-[(t-butyloxycarbonyl)amino]-4,4-dimethyl-2-oxo-1-azetidinyl sulfate, tetrabutylammonium salt for (±)-3-[(t-butyloxycarbonyl)amino]-4,4-dimethyl-2-oxo-1-azetidinyl sulfate, tetrabutylammonium salt yielded the title compound. Recrystallization of a small sample from ethanol/water gave the title compound as a crystalline solid, melting point 140°–142° (d), [60 ]D =74.8° (C =1; $H_2O$).

(K) [3S(Z)]-2-[[[1-(2-Amino-4-thiazolyl)-2-[[4,4-dimethyl-2-oxo-1-(sulfooxy)-3-azetidinyl]amino]-2-oxoethylidene]amino]oxy]-2-propenoic acid, diphenylmethyl ester, tetrabutylammonium salt To a solution of 2-amino-α-[[[1-(diphenylmethoxy)carbonyl]ethenyl]oxy]imino]-4-thiazoleacetic acid (1.423 g, 3.36 mmole) and triethylamine (0.404 g, 3.88 mmole) under argon at −30° C. was added diphenyl chlorophosphate (0.902 g, 3.36 mmole). The reaction mixture was stirred at −30° C. for one hour to form the mixed anhydride. (3S)-3-Amino-4,4-dimethyl-2-oxo-1-azetidinyl sulfate (0.706 g, 3.36 mmole) was dissolved in 4 ml of dimethylformamide at 0° C. and this solution and triethylamine (0.404 g, 3.88 mmole) were simultaneously added to the mixed anhydride solution at −30° C. The reaction mixture was slowly warmed to 0° C. over a one hour period. The reaction mixture was treated with triethylamine (0.338 g, 3.36 mmole) and then concentrated in vacuo. The residue was treated with water to yield a gum which was separated from the aqueous layer and washed with more water. The gum was dissolved in 100 ml of methylene chloride and shaken with a solution of tetrabutylammonium hydrogen sulfate (1.14 g, 3.36 mmole) in 30 ml of water. The organic phase was separated and washed three times with water, dried over sodium sulfate and evaporated to a foam. This foam was dissolved in 30 ml of methylene chloride and diluted to 120 ml with ethyl acetate. The title compound crystallized as 1.73 g of a white solid, melting point 170°–172° C.

(L)
[3S(Z)]-2-[[[1-(2-Amino-4-thiazolyl)-2-[[4,4-dimethyl-2-oxo-1-(sulfooxy)-3-azetidinyl]amino]-2-oxoethylidene]amino]oxy]-2-propenoic acid A solution of [3S(Z)]-2-[[[1-(2-amino-4-thiazolyl)-2-[[4,4-dimethyl-2-oxo-1-(sulfooxy)-3-azetidinyl]amino]-2-oxoethylidene]amino]oxy]-2-propenoic acid, diphenylmethyl ester, tetrabutylammonium salt (2.17 g, 2.54 mmole) in methylene chloride (24 ml) and anisole (1 ml) at −12° C. was treated with trifluoroacetic acid (8 ml) and the reaction mixture was stirred at -10° C. under argon for 1 hour. The mixture was treated dropwise with 60 ml of ethyl acetate and the remaining slurry stirred for 20 minutes and then filtered and washed with ethyl acetate and hexane. After drying in air, the solid was slurried with 50 ml of water at 20° C. and crystals formed within a few minutes. After crystallization, the solution was filtered and the solid washed with water and dried in vacuo to give 0.9 g of the title compound, melting point 140°–170° , dec.

EXAMPLE 3

(±)-(Z)-2-[]]1-(2-Amino-4-thiazoly)-2-oxo-2-[]2-[[2-oxo-1-(sulfooxy)-1-azaspiro[3.3]hept-3-yl]amino]ethylidene]amino]oxy]-2-propenoic acid (A)
N-(t-Butoxycarbonyl)-α-(1-hydroxycyclobutyl)glycine, benzyl ester A solution of diisopropylamine (9.7 ml, 70 mmoles) in 150 ml of dry tetrahydrofuran at −40° C. under argon was treated with 39 ml (64.5 mmoles) of 1.71N n-butyllithium in hexane and the pale yellow solution stirred at −40° C. for 20 minutes. The solution was cooled to −78° C., and a solution of 7.95 g (30 mmoles) of N-(t-butoxycarbonyl) glycine, benzyl ester in 30 ml of dry tetrahydrofuran was dripped in over 5 minutes, resulting in a dark yellow solution, and, after 20 minutes, a slight turbidity. After 0.5 hours, a solution of 2.42 g (2.0 ml, 34.5 mmoles) of cyclobutanone in 30 ml of tetrahydrofuran was added. The resulting yellow turbid mixture was stirred at −78° C. for 15 minutes, then placed in a 0° C. ice bath for 2 hours. At an internal temperature of −25° C. (1 hour), the solution became clear, and at −15° C. turned dark purple. It was stirred at 0° C. for 0.5 hours, then treated with 3.96 g (66 mmoles) of glacial acetic acid in 15 ml of tetrahydrofuran, giving a turbid, light yellow mixture. This was poured into 500 ml of cold water and extracted twice with ethyl acetate. The extracts were washed with 2% potassium bisulfate, 5% sodium bicarbonate, and brine, dried (sodium sulfate) and evaporated to a thick oil. Chromatography on 800 ml of LPS-1 in hexane:ethyl acetate (2:1) and combination of the product fractions (Rf=.29) gave 7.8 g of product as an oil. B) N-(t-Butoxycarbonyl)-α-(1-hydroxycyclobutyl)-glycine N-(t-Butoxycarbonyl)-α-(1-hydroxycyclobutyl)-glycine, benzyl ester (7.8 g, 23.3 mmoles) was hydrogenated at 1 atmosphere over 1.0 g of 10% palladium on charcoal in 150 ml of absolute ethanol for 4 hours at 25° C. The catalyst was filtered and the solvent evaporated in vacuo. Benzene was added and evaporated twice, to give 5.0 g of product as a hard foam.

(C)
N-(Benzyloxy)-Nz-(t-butoxycarbonyl)-α-(1-hydroxycyclobutyl)glycinamide

N-(t-Butoxycarbonyl)-α-(1-hydroxycyclobutyl)-glycine (5.0 g, 20.4 mmoles) was dissolved in 150 ml of dry tetrahydrofuran under argon. Hydroxybenzotriazole hydrate (3.12 g, 20.4 mmole) was added, and the mixture was chilled to 0° C., and then treated with 4.20 g (20.4 mmoles) of dicyclohexylcarbodiimide. After 1.75 hours at 0° C., a solution of 0-benzylhydroxylamine in 15 ml of tetrahydrofuran was added, and the mixture stirred at 0°–25° C. for 17 hours. The tetrahydrofuran mixture was then chilled to −10° C. for 20 minutes and the resulting solids filtered and washed with dry tetrahydrofuran. The filtrate was evaporated and the residue taken up in ethyl acetate and washed quickly with 2% potassium bisulfate, brine, 5% sodium bicarbonate, and brine, then dried (sodium sulfate) and evaporated to a foam. Trituration with isopropyl ether gave 4.69 g of product as a white solid, melting point 95°–97° C.

(D)
1-(Benzyloxy)-3-[(t-butoxycarbonyl)amino]-2-oxo-1-azaspiro[3.3]heptane

N-(Benzyloxy)-Nz-(t-butoxycarbonyl)-α-(1-hydroxycyclobutyl)glycinamide (3.50 g, 10 mmole) in 200 ml of dry tetrahydrofuran at 0° C. under argon was treated with 2.4 ml (15 mmole) of diethylazodicarboxylate, then with a solution of triphenylphosphine (5.2 g, 20 mmole) in 50 ml of tetrahydrofuran over 10 minutes, and the mixture stirred at 0° C. for one hour. The yellow color persisted so an additional 0.52 g (2 mmole) of triphenylphosphine was added. After 15 minutes, evaporation in vacuo gave an oil. Trituration with 100 ml of hexane:ethyl acetate (2:1) gave a white solid which was filtered. Chromatography of the filtrate on 800 ml of LPS-1 gave product fractions [Rf=0.8 in hexane:ethyl acetate (1:1)]contaminated with a close-running impurity which was removed by trituration with isopropyl ether, giving the product as a white solid, 1.07 g, melting point 156°–157° C.

(E)
3-[(t-Butoxycarbonyl)amino]-2-oxo-1-(sulfooxy)1-azaspiro[3.3]heptane, monosodium salt 1-(Benzyloxy)-3-[(t-butoxycarbonyl)amino]-2-oxo-1-azaspiro[3.3]heptane (1.07 g, 3.22 mmoles) was hydrogenated at 1 atmosphere in 30 ml of absolute ethanol over 0.4 g of 10% palladium on charcoal for 3 hours at 25° C. The catalyst was filtered and the solvent removed in vacuo at 10° C. to give a solid. This was taken up in 19 ml of dry pyridine and treated with 1.44 g (9 mmoles) of pyridine-sulfur trioxide at 25° C. under argon. After 4 hours, the volatiles were removed in vacuo, the residue taken up in water, and the pH (5.40) adjusted to 6.45 with dilute sodium bicarbonate. Passing through a 40 ml Dowex AG50 (K+) column in water eluted the product within 300 ml. Lyophilization gave a white solid, which was chromatographed on HP-20, first in water, then with a gradient increase of acetone (20%). Product fractions were lyophilized to give 0.75 g of product as a white powder.

(F) 3-Amino-2-oxo-1-(sulfooxy)-1-azaspiro[3.3]heptane

3-[(t-Butoxycarbonyl)amino]-2-oxo-1-(sulfooxy)-1-azaspiro[3.3]heptane, monosodium salt (0.3 g, 0.87 mmole) was slurried in 2.5 ml of dry dichloromethane and 1.0 ml of anisole at -10° C. under argon, and then treated with 4.0 ml of trifluoroacetic acid. After 0.5 hour, a solid had formed. After 1.5 hours, 4 ml of dry toluene was added, and the mixture evaporated in vacuo to give a solid, 3-amino-2-oxo-1-(sulfooxy)-1-azaspiro[3.3]heptane, which was triturated twice with hexane and dried in vacuo at 25° C. for 1 hour.

(G) (±)
-(Z)-2-[[[1-(2-Amino-4-thiazolyl)-2-oxo-2-[[2-oxo-1-(sulfooxy)-1-azaspiro[3.3]hept-3-yl]amino]ethylidene]amino]oxy]-2-propenoic acid, diphenylmethyl ester, tetrabutylammonium salt Following the procedure of Example 2, part K, but substituting 3-amino-2-oxo-1-(sulfooxy)-1-azaspiro[3.3]heptane for (3S)-3-amino-4,4-dimethyl-2-oxo-1-azetidinyl sulfate, yielded the title compound.

(H)
(±)-(Z)-2-[[]1-(2-Amino-4-thiazolyl)-2-oxo-2-[[2-oxo-1-(sulfooxy)-1-azaspiro[3.3]hept-3-yl]amino]ethylidene]amino]oxy]-2-propenoic acid.

Following the procedure of Example 2, part L, but substituting (±)-(Z)-[[[1-(2-amino-4-thiazolyl)-2-oxo-2-[[2-oxo-1-(sulfooxy)-1-azaspiro-[3.3]hept-3-yl]amino]ethylidene]amino]oxy]-2-propenoic acid, diphenylmethyl ester, tetrabutylammonium salt for [3S(Z)]-2-[[[1-(2-amino-4-thiazolyl)-2-[[4,4-dimethyl-2-oxo-1-(sulfooxy)-3-azetidinyl]amino]-2-oxoethylidene]amino]oxy]-2-propenoic acid, diphenylmethyl ester, tetrabutylammonium salt and chromatographing the precipitate from the ethyl acetate dilution on HP-20 resin instead of recrystallizing from water, yielded the title compound, melting point 170°-200° C., dec.

What is claimed is:
1. A compound having the formula

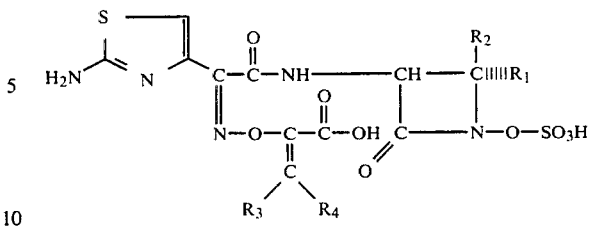

or a pharmaceutically acceptable salt thereof, wherein
$R_1$ and $R_2$ are the same or different and each is hydrogen or alkyl, or $R_1$ and $R_2$ together are —$(CH_2)_n$— wherein n is 2, 3, 4, 5 or 6; and
$R_3$ and $R_4$ are the same or different and each is hydrogen or alkyl of 1 to 3 carbon atoms.

2. A compound in accordance with claim 1 wherein $R_1$ and $R_2$ are the same or different and each is hydrogen or alkyl.

3. A compound in accordance with claim 1 wherein $R_1$ and $R_2$ are the same or different and each is hydrogen or methyl.

4. A compound in accordance with claim 1 wherein one of $R_1$ and $R_2$ is hydrogen and the other is methyl or ethyl.

5. A compound in accordance with claim 1 wherein $R_1$ and $R_2$ are each methyl.

6. A compound in accordance with claim 1 wherein $R_1$ and $R_2$ are each hydrogen.

7. A compound in accordance with claim 1 wherein $R_1$ and $R_2$ together are —$(CH_2)_n$—.

8. A compound in accordance with claim 1 wherein $R_3$ and $R_4$ are each hydrogen.

9. A compound in accordance with claim 1 wherein $R_3$ is alkyl of 1 to 3 carbon atoms and $R_4$ is hydrogen.

10. A compound in accordance with claim 1 wherein $R_3$ and $R_4$ are each alkyl of 1 to 3 carbon atoms.

11. The compound in accordance with claim 1, [3S(Z)]-2-[[[1-(2-amino-4-thiazolyl)-2-[[4,4-dimethyl-2-oxo-1-(sulfooxy)-3-azetidinyl]amino]-2-oxoethylidene]amino]oxy]-2-propenoic acid.

12. The compound in accordance with claim 1, (±)-(Z)-2-[[[1-(2-amino-4-thiazolyl)-2-oxo-2-[[2-oxo-1-(sulfooxy)-1-azaspiro[3.3]hept-3-yl]amino]ethylidene]amino]oxy]-2-propenoic acid.

* * * * *